US009964553B2

(12) United States Patent
Shin et al.

(10) Patent No.: US 9,964,553 B2
(45) Date of Patent: May 8, 2018

(54) BLOOD TESTING APPARATUS AND BLOOD TESTING METHOD THEREOF

(71) Applicant: SAMSUNG ELECTRONICS CO., LTD., Suwon-si (KR)

(72) Inventors: Im-ho Shin, Suwon-si (KR); Jong-cheol Kim, Seoul (KR); Ki-ju Lee, Suwon-si (KR); Chung-ung Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 344 days.

(21) Appl. No.: 14/669,537

(22) Filed: Mar. 26, 2015

(65) Prior Publication Data

US 2015/0272689 A1    Oct. 1, 2015

(30) Foreign Application Priority Data

Mar. 26, 2014    (KR) .................. 10-2014-0035377

(51) Int. Cl.
    *G01N 35/00*    (2006.01)
    *G05D 7/00*     (2006.01)
    (Continued)

(52) U.S. Cl.
    CPC .  *G01N 35/00584* (2013.01); *G01N 35/00069* (2013.01); *G01N 35/0092* (2013.01);
    (Continued)

(58) Field of Classification Search
    CPC ....... G01N 35/00069; G01N 35/00584; G01N 35/00732
    See application file for complete search history.

(56) References Cited

U.S. PATENT DOCUMENTS 5,851,488 A  *  12/1998  Saul ................. G01N 21/645
                                                    422/67
5,974,016 A  *  10/1999  Andrews ............... G11B 19/10
                                                    720/626
(Continued)

FOREIGN PATENT DOCUMENTS

KR      1995-0005530 B1      5/1995
WO         02/059622 A1      8/2002
(Continued)

OTHER PUBLICATIONS

Communication dated Sep. 9, 2015 issued by the European Patent Office in counterpart European Patent Application No. 15161062.3.
(Continued)

*Primary Examiner* — Paul West
(74) *Attorney, Agent, or Firm* — Sughrue Mion, PLLC

(57) ABSTRACT

A blood testing apparatus includes a loader configured to receive a test medium, the test medium including a test object to be tested; a controller configured to perform control to operate the loader to receive the test medium in response to receiving an input of a trigger signal indicating a test start in an emergency mode; a display configured to display a user interface screen indicating the emergency mode; and an analyzer configured to automatically start analysis of the test object under the control of the controller when the test medium is received.

28 Claims, 8 Drawing Sheets

(51) Int. Cl.
*A61B 5/145* (2006.01)
*A61B 5/00* (2006.01)

(52) U.S. Cl.
CPC ......... G01N 35/00732 (2013.01); G05D 7/00 (2013.01); *A61B 5/145* (2013.01); *A61B 5/7495* (2013.01); *A61B 2505/01* (2013.01); *A61B 2560/0487* (2013.01); *G01N 2035/0091* (2013.01); *G01N 2035/00316* (2013.01); *G01N 2035/00752* (2013.01); *G01N 2035/00772* (2013.01)

(56) References Cited

U.S. PATENT DOCUMENTS

| | | | | |
|---|---|---|---|---|
| 6,334,788 | B1* | 1/2002 | Sakaguchi | G11B 33/025 439/528 |
| 8,263,386 | B2* | 9/2012 | Yoo | B01L 3/502738 422/49 |
| 2004/0165314 | A1* | 8/2004 | Fujiwara | G06F 3/0611 360/133 |
| 2007/0166195 | A1 | 7/2007 | Padmanabhan et al. | |
| 2012/0078635 | A1* | 3/2012 | Rothkopf | G10L 15/30 704/270.1 |
| 2013/0171681 | A1* | 7/2013 | Shibata | G01N 1/10 435/29 |

FOREIGN PATENT DOCUMENTS

| | | |
|---|---|---|
| WO | 2006/121266 A1 | 11/2006 |
| WO | 2014/014911 A1 | 1/2014 |

OTHER PUBLICATIONS

Communication from the European Patent Office dated Jan. 11, 2016 in a counterpart European Application No. 15161062.3.

* cited by examiner

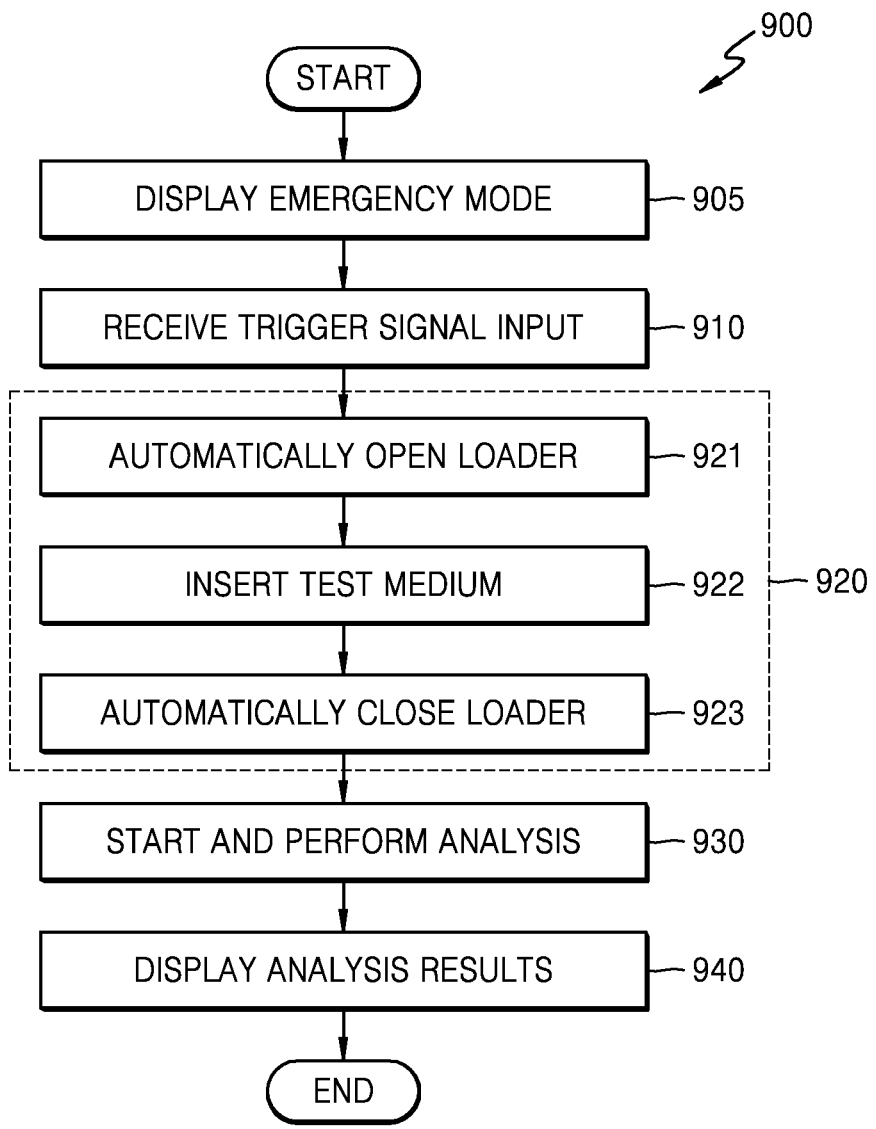

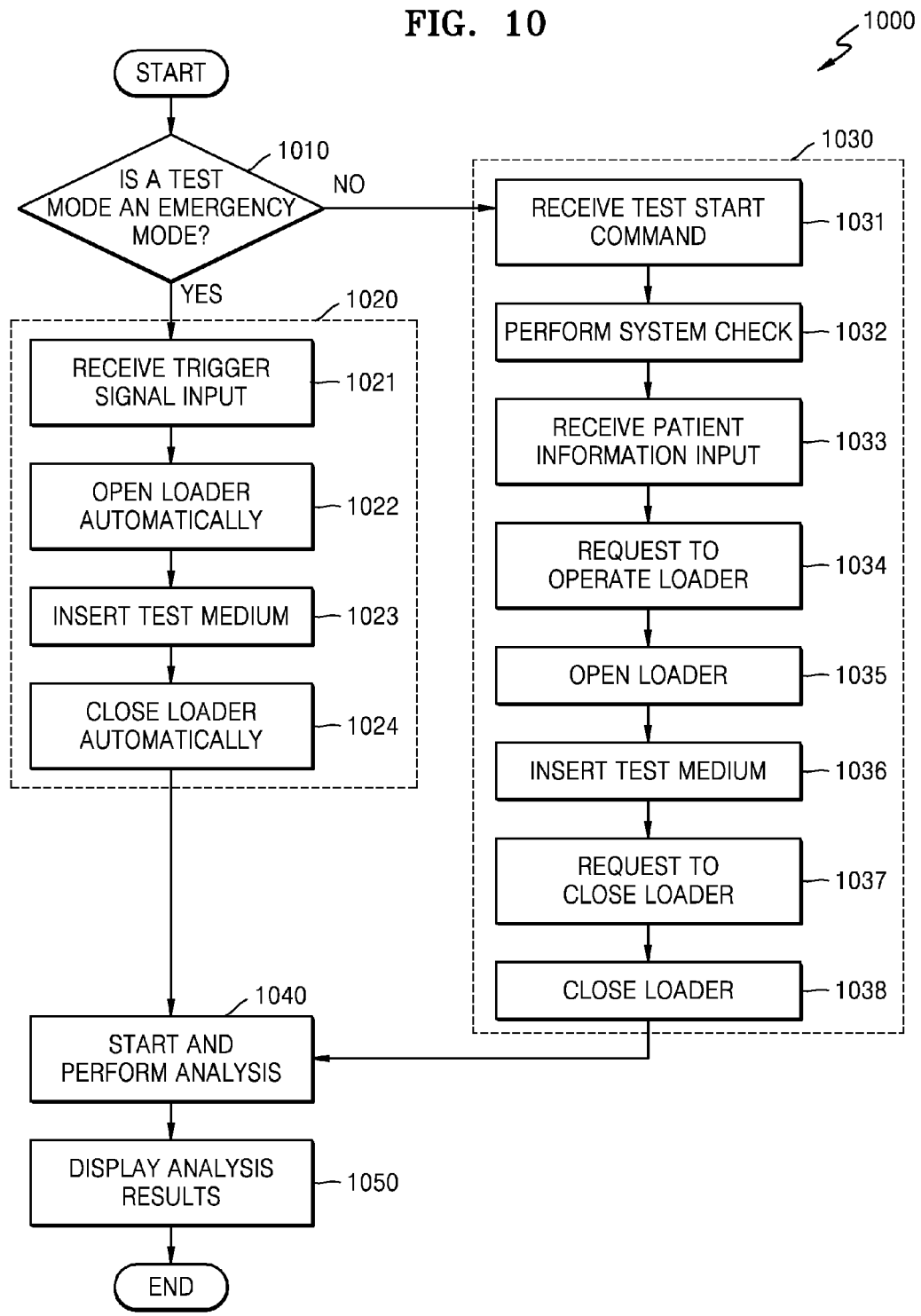

BLOOD TESTING APPARATUS AND BLOOD TESTING METHOD THEREOF

CROSS REFERENCE TO RELATED APPLICATION

This application claims priority from Korean Patent Application No. 10-2014-0035377, filed on Mar. 26, 2014, in the Korean Intellectual Property Office, the disclosure of which is incorporated herein in its entirety by reference.

BACKGROUND

1. Field

Apparatuses and methods consistent with exemplary embodiments relate to blood testing, and more particularly, to blood testing apparatuses capable of performing a blood test in an emergency and blood testing methods thereof.

2. Description of the Related Art

In a case where a patient has a medical emergency, if any diseases or health conditions of the patient are detected before the patient is transported to a medical institution, the treatment of the patient may be started more quickly when he or she reaches the medical institution.

A blood test is used as one of methods for detecting a disease of a patient.

A blood testing apparatus is widely used as an advanced diagnostic apparatus for disease detection since a heath condition of a patient may be detected from a small amount of blood that is drawn from the patient.

By using the blood testing apparatus, information about a state of a disease of a patient may be easily acquired by a relatively simple method such as blood drawing.

For example, if information about a disease of a patient is acquired by performing a blood test while transporting the patient to a medical institution, a medical treatment suitable for the disease of the patient may be started more quickly when the patient reaches the medical institution.

In the related art, a user needs to manipulate the blood testing apparatus through several operations in order to perform a blood test by using the blood testing apparatus. For example, in order to perform a blood test, the user has to operate the blood testing apparatus through various buttons of the blood testing apparatus, such as a start button, a test mode selection button, a test start button, a loading unit opening button for inputting a test medium, a loading unit closing button, and an analysis start button.

Thus, even when a patient has a medical emergency, the start of a blood test may be delayed.

Therefore, methods and apparatuses for blood testing that may perform a blood test more quickly and conveniently in the case of an emergency are needed.

SUMMARY

One or more exemplary embodiments include a blood testing apparatus capable of reducing a user operation and a blood testing method thereof.

One or more exemplary embodiments include a blood testing apparatus capable of reducing a user operation and a user input error in an emergency case and a blood testing method thereof.

Additional aspects will be set forth in part in the description which follows and, in part, will be apparent from the description, or may be learned by practice of the presented embodiments.

According to an aspect of an exemplary embodiment, a blood testing apparatus includes: a loader configured to receive an input of a test medium including a test object; a controller configured to perform control, when a trigger signal indicating a test start is input in an emergency mode, to operate the loader, receive the input of the test medium, and start analysis of the test object; a display configured to display a user interface screen indicating the emergency mode; and an analyzer configured to automatically start the analysis of the test object under the control of the controller when the test medium is input.

The controller may perform control to automatically open the loader in response to the trigger signal.

The blood testing apparatus may further include a reader configured to scan identification information corresponding to the test object, wherein the trigger signal may be generated corresponding to the identification information upon completion of the scanning of the identification information.

The blood testing apparatus may further include a user interface configured to receive a user input, wherein the trigger signal may be input through the user interface to request a test of the test object in the emergency mode.

The loader may include a detector configured to detect insertion of the test medium.

The controller may perform control to close the loader when the insertion of the test medium is detected by the detector, and may perform control to automatically start the analysis of the test object when the loader is completely closed.

The detector may include at least one of a touch sensor, an infrared sensor, a pressure sensor, and an ultrasonic sensor that detect the insertion of the test medium.

When a predetermined operation is detected after the loader is opened, the controller may determine that the test medium is inserted, and perform control to start the analysis of the test object.

The identification information may include at least one of a bar code, a quick response (QR) code, text data, a data matrix, and a recognition pattern.

The reader may include at least one of a bar code reader, a radio frequency identification (RFID) communication module, a near field communication (NFC) communication module, and an image sensor.

The test medium may include at least one of a blood test disk and a blood test cartridge.

The display may display a user interface screen indicating a test progress state of the test object under the control of the controller.

According to an aspect of an exemplary embodiment, a blood testing method includes: displaying a user interface screen indicating an emergency mode; receiving an input of a trigger signal indicating a test start in the emergency mode; receiving an input of a test medium including a test object by operating a loader of a blood testing apparatus when the trigger signal is input; and automatically starting analysis of the test object when the test medium is input.

The receiving of the input of the test medium may include: opening the loader in response to the trigger signal; and receiving the input of the test medium through the loader.

The blood testing method may further include scanning identification information corresponding to the test object by using a reader, wherein the trigger signal may be generated corresponding to the identification information upon completion of the scanning of the identification information.

The trigger signal may be for requesting a test of the test object in the emergency mode.

The receiving of the input of the test medium may include: opening the loader when the trigger signal is input; detecting insertion of the test medium; and automatically closing the loader when the insertion of the test medium is detected.

The automatic starting of the analysis of the test object may include, when a predetermined operation is detected after the loader is opened, determining that the test medium is inserted, and performing control such that the analysis of the test object is started.

The blood testing method may further include displaying a user interface screen indicating at least one of a test result and a test progress state of the test object.

According to an aspect of an exemplary embodiment, a blood testing apparatus includes: a loader configured to receive blood to be tested; and a controller configured to detect an operation mode of the blood testing apparatus, and control to automatically open the loader to receive the blood in an emergency operation mode, and opening the loader based on a user input in a normal operation mode.

The controller may automatically enter into the emergency operation mode in response to a vibration having a certain intensity or more being applied to the blood testing apparatus.

The controller may enter into the emergency operation mode in response to a command from a user.

The controller may automatically perform blood testing on the received blood in the emergency operation mode.

The blood testing apparatus may further include a display, and the controller may automatically analyze a result of the blood testing and control the display to display the analyzed result in the emergency operation mode.

The blood testing apparatus may further include a reader configured to scan identification information corresponding to the blood, and the controller may automatically perform the blood testing in response to the scanning of the identification information, in the emergency operation mode.

The identification information may include at least one of a bar code, a quick response (QR) code, text data, a data matrix, and a recognition pattern.

BRIEF DESCRIPTION OF THE DRAWINGS

The above and/or other aspects will become more apparent by describing certain exemplary embodiments with reference to the accompanying drawings, in which:

FIG. 9 is a flowchart of a blood testing method according to an exemplary embodiment; and FIG. 10 is a flowchart of a blood testing method according to an exemplary embodiment.

DETAILED DESCRIPTION

Figure 1:
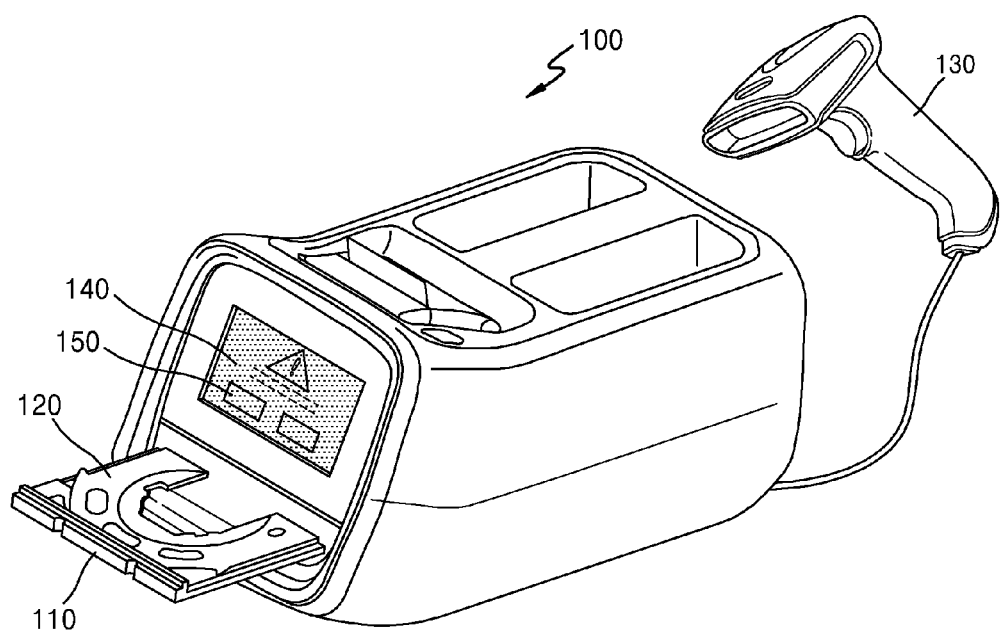
FIG. 1 is a perspective view of a blood testing apparatus according to an exemplary embodiment.

Certain exemplary embodiments are described in detail below with reference to the accompanying drawings, wherein like reference numerals refer to like elements throughout. In this regard, the exemplary embodiments may have different forms and should not be construed as being limited to the descriptions set forth herein. Accordingly, the exemplary embodiments are described below, by referring to the figures, to explain aspects of the present inventive concept. As used herein, expressions such as "at least one of," when preceding a list of elements, modify the entire list of elements and do not modify the individual elements of the list.

In the specification, when a certain portion "comprises" or "includes" a component, another component may be further included unless specified otherwise. Also, the term "unit" used herein refers to a software component or a hardware component such as a field-programmable gate array (FPGA) or an application-specific integrated circuit (ASIC), and the "unit" performs some functions. However, the "unit" is not limited to software or hardware. The "unit" may be formed so as to be in a addressable storage medium, or may be formed so as to operate one or more processors. Thus, for example, the "unit" may include components such as software components, object-oriented software components, class components, and task components, and may include processes, functions, attributes, procedures, subroutines, segments of program code, drivers, firmware, micro codes, circuits, data, a database, data structures, tables, arrays, and variables. A function provided by the components and "units" may be associated with the smaller number of components and "units", or may be divided into additional components and "units".

Also, a "user" may be, but is not limited to, a medical expert including an emergency rescuer, a doctor, a nurse, a medical laboratory technologist, a medial image expert, and a technician who repairs a medical apparatus.

FIG. 1 is a perspective view of a blood testing apparatus 100 according to an exemplary embodiment.

Referring to FIG. 1, the blood testing apparatus 100 receives an input of a test medium, which includes blood drawn from a patient, onto a loading surface 120 of a loader 110, analyzes the blood included in the test medium, and outputs results of the analysis through a display 140.

Herein, the test medium is provided to include blood that is an object to be tested. The test medium may have a disk shape, a cartridge shape, or the like. An exemplary embodiment of the test medium will be described later in detail with reference to FIG. 5.

The blood testing apparatus 100 may further include a reader 130 that may scan a signal or information indicating a test start. Herein, the signal indicating a test start may be a trigger signal indicating a test start in an emergency mode. For example, the reader 130 may include a bar code reader that may scan a bar code.

The reader 130 may include at least one of, for example, a quick response (QR) code reader, a radio frequency identification (RFID) communicator, a near field communication (NFC) communicator, and an image sensor. In detail, when information about the patient, information about the blood, or information about an emergency case number is provided in at least one of a QR code, an image, text data, and information that may be transmitted and/or received by a communication method for short distance communication such as RFID or NFC, etc., the reader 130 may scan and analyze information about the test medium.

As illustrated in FIG. 1, the blood testing apparatus 100 may have a size suitable to be mobile and portable and may be loaded into an emergency patient transportation vehicle such as an ambulance car or an ambulance helicopter.

When the blood testing apparatus 100 is loaded into an ambulance car, a vibration, a movement, or a shaking may occur in the blood testing apparatus 100 due to the movement of the ambulance car. In this case, an error may occur in operating the blood testing apparatus 100.

For example, the display 140 may have a touchscreen including a display panel and a touchpad. In this case, a user interface screen, e.g., a menu screen for performing a blood test, may be displayed on the display 140. The user may start a blood test by touching a predetermined button, for example, a button 150 included in the menu screen.

However, when a severe shaking occurs in the blood testing apparatus 100 due to the high-speed movement of the ambulance car for transportation of an emergency patient, the user may fail to touch the button 150 due to the severe shaking.

Also, since a blood test for the emergency patient needs to be completed as quickly as possible, an operation for the blood test needs to be simplified.

To acquire blood test results without a substantial delay, a possible input error in operating the blood testing apparatus 100 for the blood test needs to be avoided and the blood test operation needs to be simplified.

Therefore, according to exemplary embodiments, blood testing apparatuses and methods for reducing a possible user operation error in a blood test and quickly performing a blood test may be provided.

Figure 2:
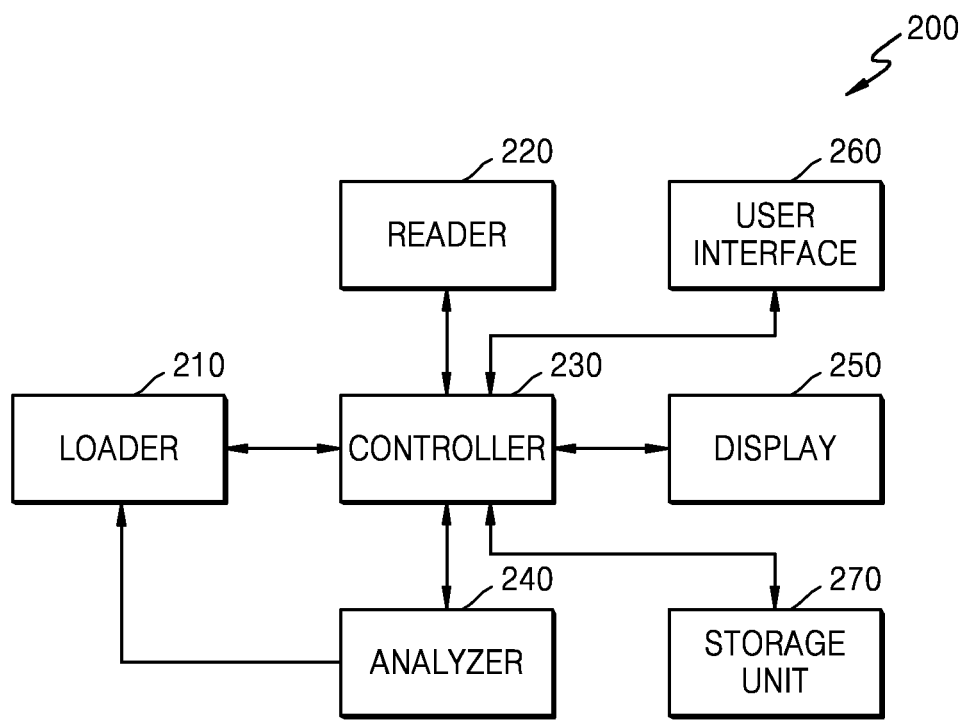
FIG. 2 is a block diagram of a blood testing apparatus according to an exemplary embodiment.

FIG. 2 is a block diagram of a blood testing apparatus 200 according to an exemplary embodiment.

Referring to FIG. 2, the blood testing apparatus 200 includes a loader 210, a controller 230, an analyzer 240, and a display 250. The blood testing apparatus 200 may further include at least one of a reader 220, a user interface 260, and a storage unit 270.

The loader 210 receives an input of a test medium. Herein, the test medium includes blood that is a test object. The loader 210 corresponds to the loader 110 illustrated in FIG. 1. The loader 210 may include a medium inserting portion for allowing insertion of a test medium to the loader 210, and the shape of the loader 210 may vary depending on test mediums.

FIG. 1 illustrates a case where the test medium has a disk shape, as an example. In this case, the loader 110 may include a disk tray, into which a disk is inserted, as a medium inserting portion.

The loader 110 may operate to draw the disk tray so that the disk may be loaded onto the disk tray.

As another example, the test medium may have a cartridge shape. In this case, the loader 210 may have a shape capable of allowing insertion of a cartridge to the loader 210.

The shape of the loader 210 may have various shapes and may vary depending on the shapes of test mediums.

When a trigger signal indicating a test start is input in an emergency mode, the controller 230 performs control to operate the loader 210, receive an input of a test medium, and start analysis of a test object included in the test medium. In an exemplary embodiment, the controller 230 may be a processor. The emergency mode is, for example, a blood test mode that reduces user manipulation to perform a blood test when an urgent blood test is required due to the medical emergency of a patient, as described above.

The controller 230 may perform control to automatically open the loader 210 in response to the trigger signal.

Herein, the trigger signal may be generated when identification information corresponding to the test object is scanned or when the user requests a test start in the emergency mode.

The display 250 displays a user interface screen indicating the emergency mode.

The analyzer 240 automatically starts analysis of the test object under the control of the controller 230 when the test medium is input to the loader 210.

The reader 220 scans the identification information corresponding to the test object. Hereinafter, the identification information corresponding to the test object is referred to as first identification information.

The first identification information is identification information of the test object included in the test medium. For example, the first identification information may include a patient name, a national insurance number of the patient, a unique identification number of the patient, a blood identification number, an emergency case number, and the like.

The first identification information may have, for example, a bar code form so that it may be quickly scanned. Also, the first identification information may have, for example, a QR code form, an image data form, or a text data form. Also, the first identification information may include a radio signal that may be transmitted through short-range communication such as RFID or NFC.

The reader 220 may include a barcode reader that may scan and interpret identification information that is provided in a bar code form. Also, the reader 220 may include a QR code reader, an image data detector, or a text data detector that may scan and interpret the identification information that is provided in a QR code, an image, or data. Also, the reader 220 may include an RFID communication module that may recognize information transmitted and/or received according to the RFID communication standard, or an NFC communication module that may recognize information transmitted and/or received according to the NFC communication standard.

Hereinafter, a case where the first identification information has a bar code form and the reader 220 is a bar code reader will be described as an example. The trigger signal may be generated in response to completion of the scanning of the first identification information.

In this case, in response to the trigger signal generated upon completion of the scanning of the first identification information, the controller 230 may perform control to operate the loader 210 and start analysis of the test object included in the test medium.

That is, in the emergency mode, the blood testing apparatus 200 automatically starts analysis of the test object upon completion of the scanning of the identification information of the test object. When the blood testing apparatus 200 is loaded into an ambulance car and is to be used for an emergency patient, an initial operation mode may be set as the emergency mode as default. Also, the user may set an operation mode of the blood testing apparatus 200 as the emergency mode.

Also, according to an exemplary embodiment, when a vibration occurs in the blood testing apparatus 200 for a predetermined period of time or more or with a predetermined intensity or more, the operation mode may be automatically converted to the emergency mode. For example, a movement or vibration may occur in the blood testing apparatus 200 for a predetermined period of time or more due to the movement of an ambulance car in the process of transportation of a patient having a medical emergency. In this case, the controller 230 of the blood testing apparatus 200 may automatically convert the operation mode to the emergency mode by detecting the movement or vibration in the blood testing apparatus 200.

The analyzer 240 analyzes the test object under the control of the controller 230. In detail, the analyzer 240 may analyze the blood, which is the test object, to generate an analysis result that may determine whether the patient has a disease.

The display 250 displays a screen. In detail, the display 250 includes a display panel and displays a screen on the display panel. In an exemplary embodiment, the display 250 may display a user interface screen associated with a blood test, for example, a screen indicating a test progress state, or a screen indicating a test result.

The user interface 260 generates and outputs a user interface screen for receiving an input of a command or data from the user, and receives an input of a command or data from the user through the user interface screen. Also, the user interface screen output from the user interface 260 may be output to the display 250 under the control of the controller 230. That is, the display 250 may display the user interface screen. Based on the user interface screen displayed on the display 250, the user may recognize information output on the user interface screen and input a command or data through the user interface screen.

For example, the user interface 260 may include a mouse, a keyboard, or an input unit including keys for receiving data input. For example, the user may input data or a command by operating at least one of the mouse, the keyboard, and the input unit included in the user interface 260.

Also, the user interface 260 may include a touchpad. In detail, the user interface 260 may include a touchpad coupled to a display panel included in the display 250, and the user interface 260 may output a user interface screen onto the display panel. Also, when a user inputs a command through the user interface screen, the touchpad may detect and recognize the input command.

In a case where the user interface 260 includes a touchpad, when the user touches a point on the user interface screen, the user interface 260 detects the touched point. Also, the user interface 260 may transmit detected information about the touched point to the controller 230. When a menu is displayed at the touched point, the controller 230 may recognize a user request or command corresponding to the menu displayed at the detected point and perform the recognized user request or command.

Hereinafter, for illustrative purposes, a case where the user interface 260 includes a touchscreen will be described as an example. In this case, a user interface screen is output through the display 250 and a user command is received through the touchscreen.

The user interface 260 may receive a user input for a test start request in the emergency mode. In this case, a trigger signal may be a signal that is input through the user interface 260 to request a test of the test object in the emergency mode. That is, the trigger signal may be generated in response to the user input. In a case where the trigger signal is generated in response to the user input, when a signal for requesting a test of the test object is input through the user interface 260 in the emergency mode, the controller 230 may recognize the input signal as the trigger signal, operate the loader 210, receive an input of the test medium, and perform control to start analysis of the test object.

The storage unit 270 may store various data and a program for performing a blood test. The storage unit 270 may include at least one storage medium from among a flash memory-type storage medium, a hard disk-type storage medium, a multimedia card micro-type storage medium, a card-type memory (e.g., a secure digital (SD) card, an extreme digital (XD) memory, and the like), a random access memory (RAM), a static random access memory (SRAM), a read-only memory (ROM), an electrically erasable programmable read-only memory (EEPROM), a programmable read-only memory (PROM) magnetic memory, a magnetic disk, and an optical disk. For example, the storage unit 270 may store a blood test process and a test result.

Figure 3:
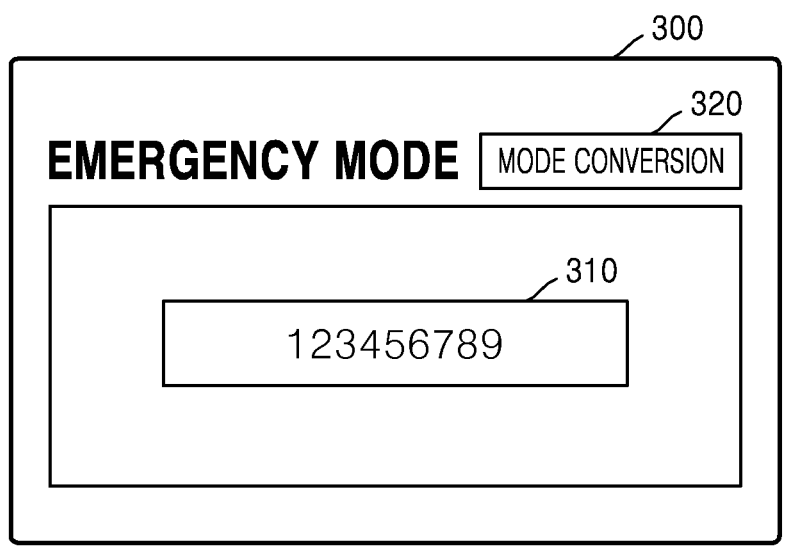
FIG. 3 is a diagram illustrating an example screen displayed in a blood testing apparatus according to an exemplary embodiment.

FIG. 3 is a diagram illustrating an example screen displayed in the blood testing apparatus 200 of FIG. 2.

Referring to FIG. 3, the display 250 may display a user interface screen 300 indicating the emergency mode. Also, the user interface screen 300 may further include a menu window 310 and a mode conversion menu 320, which will be described in detail later.

Figure 4:
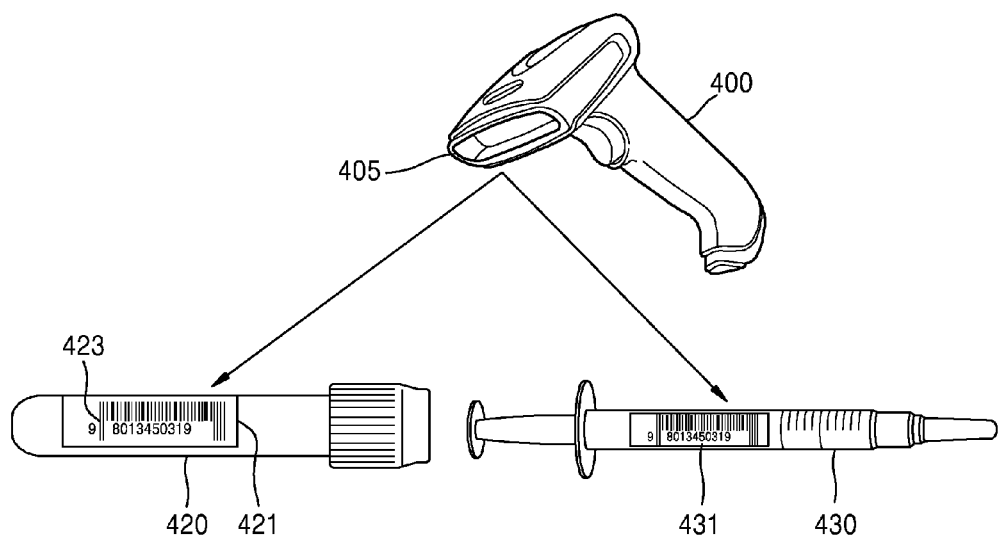
FIG. 4 is a diagram illustrating an operation of a blood testing apparatus according to an exemplary embodiment.

FIG. 4 is a diagram illustrating an operation of the blood testing apparatus 200 of FIG. 2. Since a bar code reader 400 illustrated in FIG. 4 corresponds to the reader 220 of FIG. 2, a redundant description thereof will be omitted herein.

Hereinafter, a case where a blood test is performed in the process of transporting an emergency patient will be described as an example.

For example, when blood is drawn from a patient, the drawn blood is stored in a blood tube 420. First identification information 421 for identification of blood, which is a test object, may be attached to the blood tube 420. As described above, the first identification information may include a patient name, a national insurance number of the patient, a unique identification number of the patient, a blood identification number, an emergency case number, and the like.

In an exemplary embodiment, the first identification information may be separately provided without being attached to the blood tube 420. The first identification information may be provided as a separate sticker or a separate document without being attached to the blood tube 420.

Also, in an exemplary embodiment, first identification information 431 may be attached to a syringe 430 that is used to draw blood from the patient.

The bar code reader 400 includes a scanner 405. The scanner 405 scans the first identification information 421. For example, the scanner 405 may scan a bar code 423 included in the first identification information 421. The scanned information is transmitted to the controller 230.

When the scanning of the first identification information 421 by the bar code reader 400 is completed, the controller 230 starts a blood test as described above. In detail, when the analysis of the scanned first identification information 421 is completed, the controller 230 may acquire information for identification of blood to be tested. The controller 230 may start a blood test upon acquiring the first identification information 421 of the blood.

In detail, upon completion of the scanning, the controller 230 performs control to open the loader 210. For example, the controller 230 may perform control to draw the disk tray and load the blood test disk, which is the test medium, on the disk tray.

When the test medium is loaded on the disk tray, the controller 230 may perform control to close the loader 210. When the loader 210 is completely closed, the controller 230 may perform control to start analysis of the test object.

Also, the loader 210 may further include a detector that detects insertion of the test medium. In detail, the detector may include a detecting sensor that detects insertion of the test medium into the loader 210. Herein, the detecting sensor may include, but not limited to, a touch sensor, an infrared sensor, a pressure sensor, and an ultrasonic sensor.

When the detector includes an infrared sensor, a pressure sensor, and an ultrasonic sensor, the detector may detect when the test medium is loaded on the disk tray.

Also, when a predetermined operation is detected after the loader 210 is opened, the controller 230 may determine that the test medium including the test object is inserted, and perform control to start analysis of the test object. For example, when the user touches the loader 210 a predetermined number of times or presses the disk tray of the loader 210 into the blood testing apparatus 200 after the loader is opened, the controller 230 may determine that the test medium is inserted into the loader 210.

For example, in a case where the detector includes a touch sensor or a pressure sensor at a portion where a user operation occurs, when the user inserts a disk onto the disk tray and touches the disk tray two times during the insertion, the controller 230 may detect a user touch detected by the touch sensor and determine that the disk is inserted.

Figure 5:
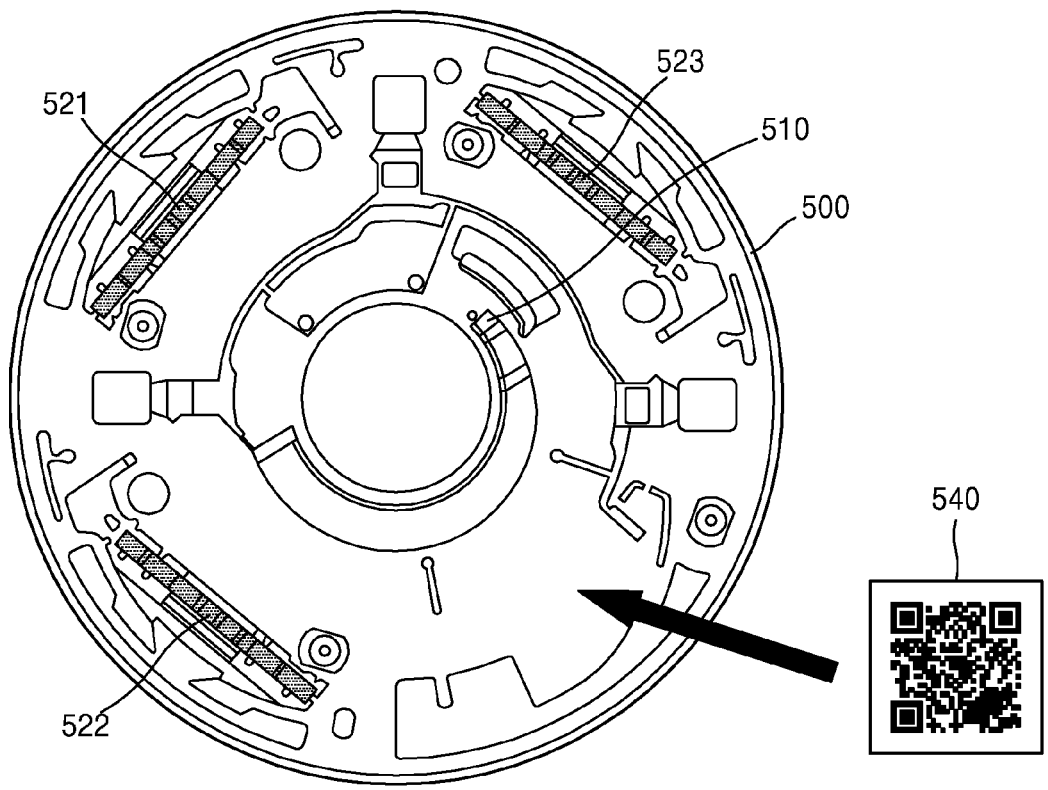
FIG. 5 is a diagram illustrating a test medium used in a blood testing apparatus according to an exemplary embodiment.

FIG. 5 is a diagram illustrating the test medium used in the blood testing apparatus 200 of FIG. 2.

When the test medium includes a blood test disk, the blood test disk may be configured as illustrated in FIG. 5, according to an exemplary embodiment.

Referring to FIG. 5, blood drawn from the patient is inserted through an insertion hole 510 of a blood test disk 500 that is a test medium. The inserted blood spreads into one or more strips 521, 522, and 523 included in the blood test disk 500.

Also, the blood test disk 500 may include second identification information 540 for identification of the test medium. As illustrated in FIG. 5, the second identification information 540 may include a QR code and attached to a portion of the blood test disk 500. For example, the second identification information 540 may be attached to a front side of the blood test disk 500.

The analyzer 240 analyzes blood included in the test medium. In detail, the analyzer 240 may perform an accurate analysis of blood existing in the strips 521, 522, and 523 in the blood test disk 500.

The analyzer 240 may perform a test by using the blood. Based on the second identification information 540, the analyzer 240 may perform a test to determine a disease. Also, based on user settings or initial settings of the blood testing apparatus 200, the analyzer 240 may perform a test to determine a disease.

For example, the analyzer 240 may perform a troponin I (TnI) test by using the blood that is the test object. Herein, the TnI test is a cardiac marker test that is used to diagnose an acute coronary syndrome (ACS) including an acute myocardial infarction (AMI). In the event of an emergency related to a myocardial infarction, a TnI test may need to be performed as a cardiac marker test. The TnI is a myocardial injury index and appears in blood when a myocardial tissue is injured. As described above, in the case of a patient with a heart disorder having a medical emergency, it is important to perform a diagnosis and a treatment within a short time. Therefore, it is desirable to complete a TnI test, that is, a blood test, before the emergency patient reaches a medical institution.

As in the above example, in a case where a blood test is performed in the process of transporting a patient, the analyzer 240 may perform a TnI test to diagnose a disease of the patient having a medical emergency. In an exemplary embodiment, the controller 230 may automatically perform a TnI test upon completion of the scanning of the first identification information.

Also, the controller 230 may control the display 250 to display a user interface screen indicating a blood test process and a blood test result. Example screens, which may be displayed in the process of a blood test, will be described below in detail with reference to FIGS. 6A, 6B, and 6C.

Figure 6A:
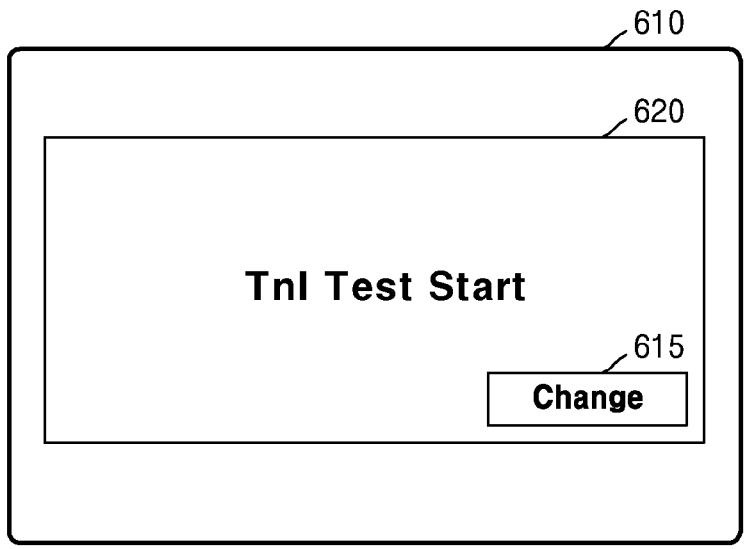
FIGS. 6A, 6B, and 6C are diagrams illustrating example screens displayed in a blood testing apparatus according to an exemplary embodiment.
Figure 6B:
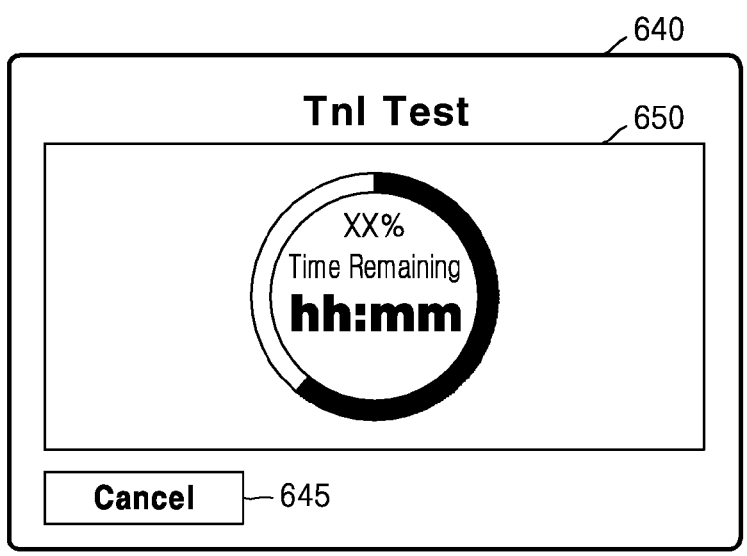
Figure 6C:
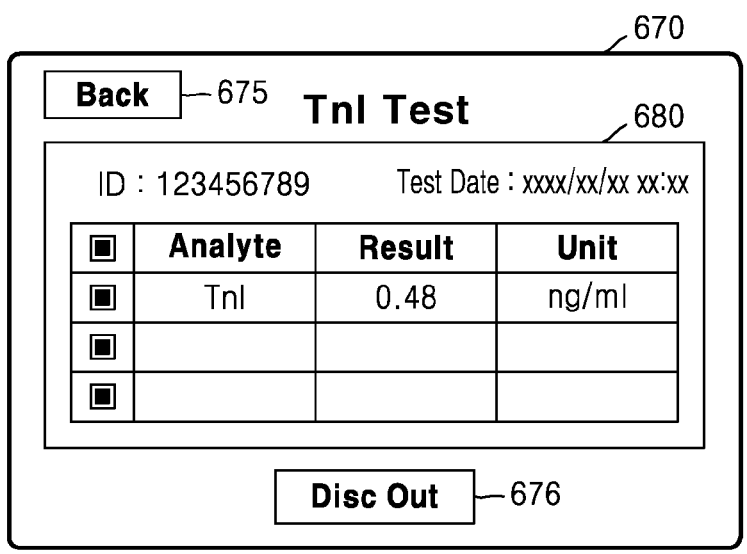

FIGS. 6A to 6C are diagrams illustrating example screens displayed in the blood testing apparatus 200 of FIG. 2.

Referring again to FIG. 3, when the screen 300 indicating the emergency mode is displayed and the first identification information is scanned by the reader 220, the scanned and analyzed first identification information may be indicated in the menu window 310. FIG. 3 illustrates a case where the first identification information includes a blood identification number "123456789", which is displayed on the menu window 310.

When the scanning of the first identification information is completed, the controller 230 starts analysis of blood that is a test object.

Referring to FIG. 6A, the controller 230 may output a user interface screen 610 indicating a start of a test. Referring to FIG. 6A, the test may be a TnI test. The user interface screen 610 may include a screen 620 indicating a start of a TnI test. Also, the user may change a test item by using a test item change menu 615 included in the user interface screen 610.

Also, the controller 230 may perform control such that a plurality of tests are sequentially performed according to initial settings.

The controller 230 may perform control to output a user interface screen 640 indicating a progress state of the test.

Referring to FIG. 6B, the controller 250 may display a user interface screen 640 indicating the progress of a TnI test. The user interface screen 640 may include a screen 650 indicating a test progress that is, for example, a completion progress percentage of the TnI test. For example, the screen 650 may indicate a remaining time left to accomplish the blood test, as shown in FIG. 6B.

Also, the user interface screen 640 may further include a menu for stopping or canceling a test, for example, a cancel menu 645 for requesting a test cancelation. Thus, even when a test is automatically performed upon completion of the scanning by the scanner 405, the controller 230 may stop or cancel the performance of the test according to a user request.

Also, when a test is completed by the analyzer 240, the controller 230 may perform control to display a test result output from the analyzer 240.

Referring to FIG. 6C, under the control of the controller 230, the display 250 may display a user interface screen 670 including a test result 680.

Also, the user interface screen 670 may further include a menu 676 for requesting the unloading of a blood test disk that is a test medium. Additionally, the user interface screen 670 may further include a menu 675 for switching a screen to a previously displayed screen.

Also, user interface screens illustrated in FIGS. 6A, 6B, and 6C may be automatically switched and displayed according to the progress of a blood test even without a separate user request.

Figure 7:
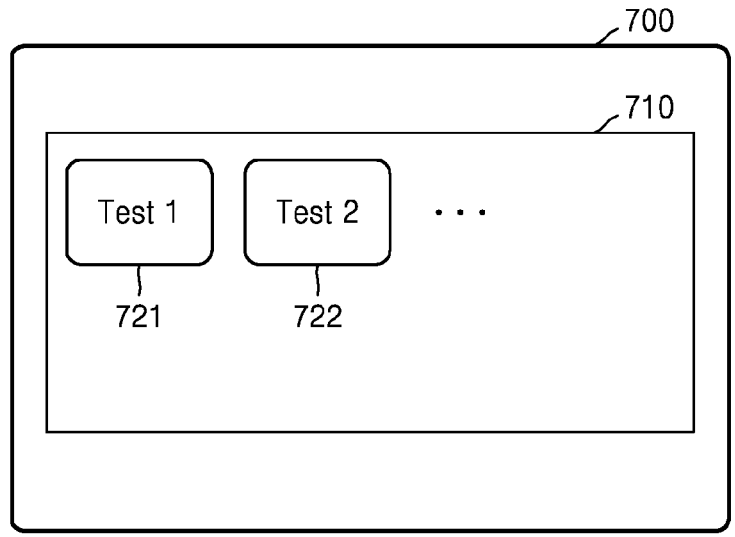
FIG. 7 is a diagram illustrating an example screen displayed in a blood testing apparatus according to an exemplary embodiment.

FIG. 7 is a diagram illustrating an example screen displayed in the blood testing apparatus 200 of FIG. 2.

A test performed in the emergency mode may be set in advance, according to an exemplary embodiment. When the scanning of the first identification information is completed, a test may be performed by using a user interface screen 700 that is output in response to the completion of the first identification information.

Referring to FIG. 7, the user interface 700 may include a list 710 including first and second test items 721 and 722 that may be performed by the blood testing apparatus 200. The user may select at least one test through the user interface screen 700. The controller 230 may control performing of the selected test.

For example, when the scanning of the first identification information is completed, the controller 230 performs control to output the user interface screen 700, and when the first test item 721 is selected by the user, the controller 230 performs control to perform a first test corresponding to the first test item 721. In an exemplary embodiment, the controller 230 may perform control to automatically open and/or close the loader 210 to receive an input of the test medium and may control to perform the first test to output a test result even without an input through a separate operation button.

Figure 8:
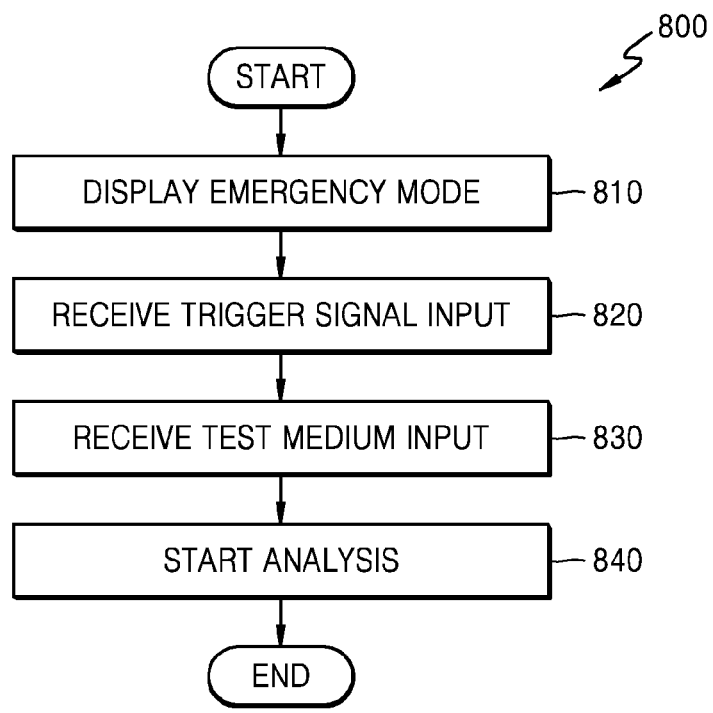
FIG. 8 is a flowchart of a blood testing method according to an exemplary embodiment.

FIG. 8 is a flowchart of a blood testing method 800 according to an exemplary embodiment. The blood testing method 800 may be performed by the blood testing apparatus 200 described with reference to FIGS. 1 to 7. Thus, redundant descriptions thereof will be omitted herein. The blood testing method 800 will be described below in detail with reference to the blood testing apparatus 200 of FIG. 2.

Referring to FIG. 8, the blood testing method 800 performs a blood test by using the blood testing apparatus 200 that receives an input of the test medium through the loader 210.

Referring to FIG. 8, the blood testing method 800 displays a user interface screen indicating an emergency mode (operation 810). Operation 810 may be performed by the display 250 under the control of the controller 230.

An input of a trigger signal indicating a test start is received in the emergency mode (operation 820). Operation 820 may be performed according to the scanning of the first identification information by the reader 220, or may be performed according to the user input received through the user interface 260.

For example, the reader 220 may scan the first identification information that is identification information corresponding to the test object. When the scanning operation is completed, a trigger signal may be generated accordingly and input to the controller 230. In this case, the trigger signal may be generated in response to the first identification information upon completion of the scanning of the first identification information.

As another example, when a signal for requesting a test of the test object in the emergency mode is input through the user interface 260, the signal may be received as the trigger signal. In this case, the trigger signal may be a signal requesting a test of the test object in the emergency mode.

When the trigger signal is input, the loader 210 of the blood testing apparatus 200 is operated to receive an input of the test medium (operation 830). Operation 830 may be performed by the loader 210 under the control of the controller 230.

Next, analysis of the test object included in the test medium is started (operation 840). Operation 840 may be performed by the analyzer 240 under the control of the controller 230.

FIG. 9 is a flowchart of a blood testing method 900 according to an exemplary embodiment. Operations 905, 910, 920, and 930 of FIG. 9 respectively correspond to operations 810, 820, 830, and 840 of FIG. 8. Also, the blood testing method 900 may be performed by the blood testing apparatus 200 described with reference to FIGS. 1 to 7. Thus, redundant descriptions thereof will be omitted herein. The blood testing method 900 will be described below in detail with reference to the blood testing apparatus 200 of FIG. 2.

Referring to FIG. 9, the blood testing method 900 displays a screen indicating a test mode (operation 905). In an exemplary embodiment, as illustrated in FIG. 3, a user interface screen indicating that a test mode of the blood testing apparatus 200 is an emergency mode may be displayed. Operation 905 may be performed by the display 250 under the control of the controller 230.

Next, an input of a trigger signal indicating a test start is received in the emergency mode (operation 910). Operation 910 may be performed according to the scanning of the first identification information by the reader 220, or may be performed according to the user input received through the user interface 260.

When the trigger signal is input, the loader 210 of the blood testing apparatus 200 is operated to receive an input of the test medium (operation 920). Operation 920 may be performed by the loader 210 under the control of the controller 230.

In an exemplary embodiment, when the trigger signal is input, the loader 210 of the blood testing apparatus 200 is automatically opened in response to the trigger signal (operation 921). Next, an input of the test medium is received through the opened loader 210 (operation 922).

Next, when insertion of the test medium is detected, the loader 923 is automatically closed (operation 923).

Next, analysis of the test object included in the test medium is started and performed (operation 930). Operation 930 may be performed by the analyzer 240 under the control of the controller 230.

Operation 930 may further include an operation of displaying a user interface screen 640 indicating the progress of a blood test.

When the analysis of operation 930 is completed, a user interface screen, e.g., the user interface screen 670, as shown in FIG. 6C, including a blood analysis result that is a test result is displayed (operation 940). Operation 940 may be performed by the display 250 under the control of the controller 230.

FIG. 10 is a flowchart of a blood testing method 1000 according to an exemplary embodiment. Operations 1021, 1022, 1023, 1024, 1040, and 1050 of FIG. 10 respectively correspond to operations 910, 921, 922, 923, 930, and 940 of FIG. 9. Also, the blood testing method 1000 may be performed by the blood testing apparatus 200 described with reference to FIGS. 1 to 7. Thus, redundant descriptions thereof will be omitted herein. The blood testing method 1000 will be described below in detail with reference to the blood testing apparatus 200 of FIG. 2.

Referring to FIG. 10, the blood testing method 1000 determines whether a test mode is an emergency mode (operation 1010). Operation 1010 may be performed by the controller 230.

In operation 1010, the blood testing apparatus 200 may be set to operate in a predetermined mode by initial setting. For example, in the case of the blood testing apparatus 200 loaded on an emergency patient transportation vehicle such as an ambulance car, the user may set the operation mode of the blood testing apparatus 200 to the emergency mode through an initial setting. As another example, when a vibration occurs in the blood testing apparatus 200 for a predetermined time or more or with a predetermined intensity or more, the operation mode of the blood testing apparatus 200 may be automatically converted into the emergency mode.

Also, the user interface screen 300 may further include the mode conversion menu 320 for converting the emergency mode into a normal mode, and vice versa. Herein, the normal mode is an operation mode in which a blood test is started and performed according to a user operation regardless of the scanning of the first identification information.

When the test mode is the emergency mode, operation 1020, including operations 1021 to 1024, operation 1040, and operation 1050 are performed. As described above, operations 1021 to 1050 respectively correspond to operations 910 to 940 of FIG. 9.

When the test mode is the normal mode, operation 1030 are performed.

In detail, when the operation mode of the blood testing apparatus 200 is the normal mode, a test start command is received (operation 1031). Operation 1031 may be performed by the controller 230. In detail, the blood testing apparatus 200 outputs a user interface screen for starting and performing a test. Next, the user may touch a menu for requesting a test start through the user interface screen.

When the test start command is received (operation 1031), the controller 230 performs a system check (operation 1032).

When the system check is completed, the blood testing apparatus 200 receives an input of patient information (operation 1033). For example, the user may directly input the patient information through the user interface screen that is output through the display 250. As another example, patient information including at least one of a code, an image, and a text may be scanned and analyzed through the reader 220.

When the input of the patient information is completed, a request for operating the loader 210 is received (operation 1034). In detail, the user may input a request for opening the loader 210 through the user interface screen.

Accordingly, the loader 210 is opened (operation 1035), and the test medium is inserted (operation 1036).

When the test medium is inserted, the user may input a request for closing the loader 210 through the user interface screen (operation 1037).

Accordingly, the loader 210 is closed (operation 1038).

Next, the user inputs a command for requesting a test start through the user interface screen. Accordingly, analysis of the test object is started and performed (operation 1040).

As described above, according to the one or more of the above exemplary embodiments, in the emergency mode, the user operation for performing the blood test may be reduced so that the blood test may be performed quickly and conveniently. On the other hand, in the normal mode, sequential user operations are requested to perform the blood test. That is, several user operations are required for completion of a test.

As described above, the blood testing apparatus and method according to the exemplary embodiments automatically perform a blood test when identification information of the test object is scanned.

Accordingly, a user operation for performing a blood test may be reduced and a possible input error in the user operation may be reduced accordingly, so that a blood test result may be quickly acquired.

Also, according to the exemplary embodiments, by scanning and acquiring the identification information of the test object, it is possible to reduce an information input error and an information input delay that may occur due to vibration or shaking of an emergency transportation vehicle when a user interface such as a touchscreen is used.

Also, according to the exemplary embodiments, by automatically starting a test upon completion of the scanning of the identification information of the test object, the user operation for performing the blood test may be reduced and thus the blood test may be quickly performed.

The exemplary embodiments may be written as computer programs and may be implemented in general-use digital computers that execute the programs using a computer-readable recording medium.

Examples of the computer-readable recording medium include magnetic storage media (e.g., ROMs, floppy disks, hard disks, etc.), optical recording media (e.g., compact disk (CD)-ROMs, digital versatile disks (DVDs), etc.), and transmission media such as Internet transmission media.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art

What is claimed is:

1. A blood testing apparatus comprising:
   a loader configured to be open or closed and to receive a test medium including a test object to be tested;
   a controller configured to determine an operation mode of the blood testing apparatus among a normal mode and an emergency mode, to control the loader to be automatically open or closed in the emergency mode, and control the loader to be opened based on a user input in the normal mode; and
   an analyzer configured to automatically start analysis of the test object under the control of the controller in the emergency mode.

2. The blood testing apparatus of claim 1, wherein the controller is configured to enter into the emergency mode in response to receiving an input of a trigger signal.

3. The blood testing apparatus of claim 1, further comprising a reader configured to scan identification information corresponding to the test object,
   wherein the controller is configured to enter into the emergency mode in response to completion of scanning of the identification information.

4. The blood testing apparatus of claim 3, wherein the identification information comprises at least one of a bar code, a quick response (QR) code, text data, a data matrix, and a recognition pattern.

5. The blood testing apparatus of claim 3, wherein the reader comprises at least one of a bar code reader, a radio frequency identification (RFID) communicator, a near field communication (NFC) communicator, and an image sensor.

6. The blood testing apparatus of claim 1, further comprising a user interface,
   wherein the controller is configured to enter into the emergency mode in response to receiving an input through the user interface, requesting a test of the test object in the emergency mode.

7. The blood testing apparatus of claim 1, wherein the loader comprises a detector configured to detect insertion of the test medium into the loader.

8. The blood testing apparatus of claim 7, wherein the controller is configured to perform control to close the loader when the insertion of the test medium is detected by the detector, and perform control to automatically start the analysis of the test object when the loader is closed.

9. The blood testing apparatus of claim 7, wherein the detector comprises at least one of a touch sensor, an infrared sensor, a pressure sensor, and an ultrasonic sensor.

10. The blood testing apparatus of claim 1, wherein, when a certain operation is detected after the loader is opened, the controller is configured to determine that the test medium is inserted, and perform control to automatically start the analysis of the test object.

11. The blood testing apparatus of claim 1, wherein the test medium comprises at least one of a blood test disk and a blood test cartridge.

12. The blood testing apparatus of claim 1, further comprising a display configured to display a first user interface screen indicating the emergency mode.

13. The blood testing apparatus of claim 12, wherein the display is configured to display a second user interface screen indicating a test progress state of the test object.

14. A blood testing method comprising:
determining an operation mode of a blood testing apparatus among a normal mode and an emergency mode;
controlling a loader of the blood testing apparatus to be automatically open or closed in the emergency mode to receive a test medium, and controlling the loader to be opened based on a user input in the normal mode, the test medium including a test object to be tested; and
automatically starting analysis of the test object in the emergency mode.

15. The blood testing method of claim 14, further comprising entering into the emergency mode in response to receiving an input of a trigger signal.

16. The blood testing method of claim 15, wherein the trigger signal is generated in response to a request for a test of the test object in the emergency mode.

17. The blood testing method of claim 14, further comprising:
scanning identification information corresponding to the test object by using a reader; and
entering into the emergency mode in response to completion of the scanning of the identification information.

18. The blood testing method of claim 14, wherein the controlling the loader comprises, in the emergency mode:
detecting insertion of the test medium to the loader; and
automatically closing the loader in response to detection of insertion of the test medium.

19. The blood testing method of claim 14, wherein the automatically starting the analysis of the test object comprises, when a certain operation is detected after the loader is opened, determining that the test medium is inserted into the loader, and performing control such that the analysis of the test object is automatically started.

20. The blood testing method of claim 14, further comprising displaying a user interface screen indicating the emergency mode.

21. The blood testing method of claim 14, further comprising displaying a user interface screen indicating at least one of a test result and a test progress state of the test object.

22. A non-transitory computer-readable recording medium having recorded thereon a program, which, when executed by a computer, causes the computer to perform the method of claim 14.

23. A blood testing apparatus comprising:
a loader configured to be opened or closed to receive a blood sample to be tested; and
a controller configured to determine an operation mode of the blood testing apparatus among a normal operation mode and an emergency operation mode, to control to automatically open or close the loader to receive the blood sample in the emergency operation mode, and to open the loader based on a user input in the normal operation mode.

24. The blood testing apparatus of claim 23, wherein the controller is configured to automatically enter into the emergency operation mode in response to a vibration having a certain intensity or more being applied to the blood testing apparatus.

25. The blood testing apparatus of claim 23, wherein the controller is configured to enter into the emergency operation mode in response to a command from a user.

26. The blood testing apparatus of claim 23, wherein the controller is configured to automatically perform blood testing on the received blood sample in the emergency operation mode.

27. The blood testing apparatus of claim 26, further comprising a display,
wherein the controller is configured to automatically analyze a result of the blood testing and control the display to display the analyzed result in the emergency operation mode.

28. The blood testing apparatus of claim 26, further comprising:
a reader configured to scan identification information corresponding to the blood sample,
wherein the controller is configured to automatically perform the blood testing in response to scanning of the identification information, in the emergency operation mode.

* * * * *